US00PP29625P2

(12) United States Plant Patent
Sakamoto

(10) Patent No.: US PP29,625 P2
(45) Date of Patent: Aug. 28, 2018

(54) ***HYDRANGEA* PLANT NAMED 'KEIKO'**

(50) Latin Name: *Hydrangea macrophylla*
Varietal Denomination: Keiko

(71) Applicant: Tiamchai Phimma, Kiryu (JP)

(72) Inventor: Shoji Sakamoto, Kiryu (JP)

( * ) Notice: Subject to any disclaimer, the term of this patent is extended or adjusted under 35 U.S.C. 154(b) by 42 days.

(21) Appl. No.: 15/530,841

(22) Filed: Mar. 7, 2017

(51) Int. Cl.
*A01H 5/02* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Hydrangea* plant named 'Keiko', characterized by its double-type, modified lacecap inflorescences, having light pink-colored sterile florets with a darker pink picotee color pattern, dark green-colored foliage, and moderately vigorous, compact-upright growth habit, is disclosed.

1 Drawing Sheet

Latin name of genus and species of plant claimed: *Hydrangea macrophylla.*
Variety denomination: 'Keiko'.

BACKGROUND OF THE INVENTION

The present invention relates to a new and distinct cultivar of *Hydrangea* plant botanically known as *Hydrangea macrophylla* and hereinafter referred to by the cultivar name 'Keiko'.

The new cultivar originated in a controlled breeding program in Kiryu-shi, Japan during June 2011. The objective of the breeding program was the development of *Hydrangea* cultivars that have double-type florets with a picotee flower color pattern and a compact-upright growth habit.

The new *Hydrangea* cultivar is the result of cross-pollination. The female (seed) parent of the new cultivar is a proprietary *Hydrangea macrophylla* breeding selection coded KD10, not patented, characterized by its double-type, lacecap, medium pink-colored inflorescences, dark green-colored foliage, and moderately vigorous, compact-upright growth habit. The male (pollen) parent of the new cultivar is a proprietary *Hydrangea macrophylla* breeding selection coded K15, not patented, characterized by its single-type, lacecap, pink-colored inflorescences having a picotee flower color pattern, dark green-colored foliage, and moderately vigorous, compact-upright growth habit. The new cultivar was discovered and selected as a single flowering plant within the progeny of the above stated cross-pollination during April 2013 in a controlled environment in in Kiryu-shi, Japan.

Asexual reproduction of the new cultivar by softwood cuttings since June 2014 in Kiryu-shi, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Keiko' as a new and distinct cultivar of *Hydrangea* plant:

1. Double-type, modified lacecap inflorescences, having light pink-colored sterile florets with a darker pink picotee color pattern;
2. Dark green-colored foliage; and
3. Moderately vigorous, compact-upright growth habit.

Plants of the new cultivar differ from plants of the female parent primarily in having a picotee flower color pattern. Plants of the new cultivar differ from plants of the male parent primarily in having a double-type flower.

Of the many commercially available *Hydrangea* cultivars, the most similar in comparison to the new cultivar is 'Posy-Bouquet Noble II', not patented. However, in comparison, plants of the new cultivar differ from plants of 'Posy-Bouquet Noble II' in at least the following characteristics:

1. Plants of the new cultivar have florets with a picotee color pattern unlike plants of 'Posy-Bouquet Noble II';
2. Plants of the new cultivar have a more compact growth habit than plants of 'Posy-Bouquet Noble II'; and
3. Plants of the new cultivar have darker green-colored foliage than plants of 'Posy-Bouquet Noble II'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Keiko'. The plants were approximately one-year old and were grown in one-gallon containers in a poly-covered greenhouse in Kiryu-shi, Japan. Plants were given one pinch at transplant.

DETAILED BOTANICAL DESCRIPTION

Figure 1:
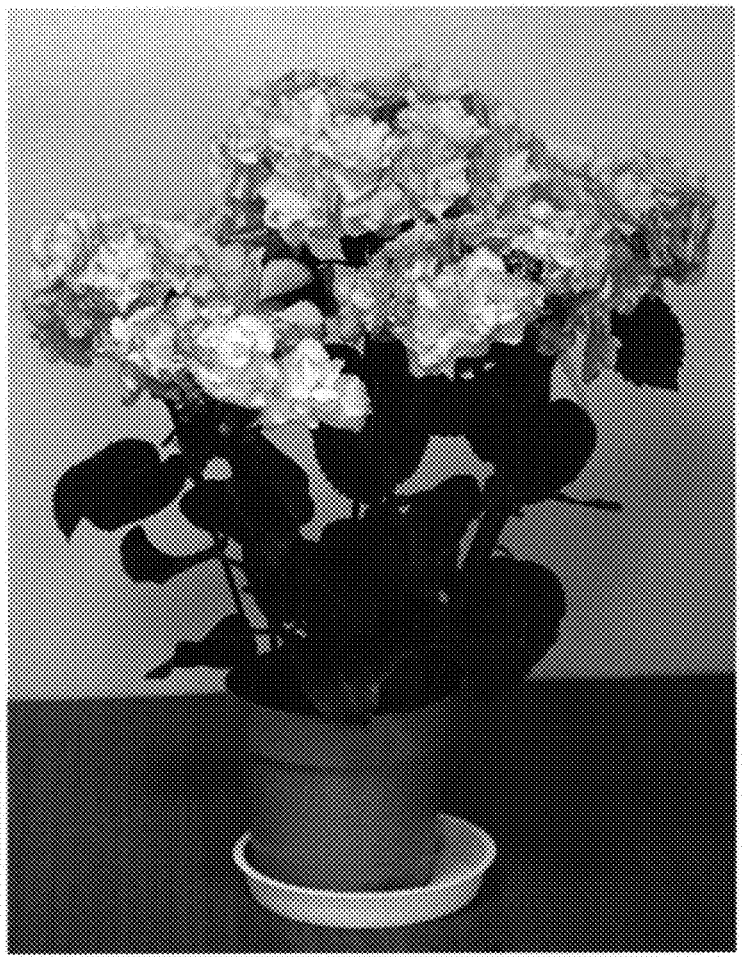
FIG. 1 illustrates a side view of the overall growth and flowering habit of 'Keiko'.
Figure 2:
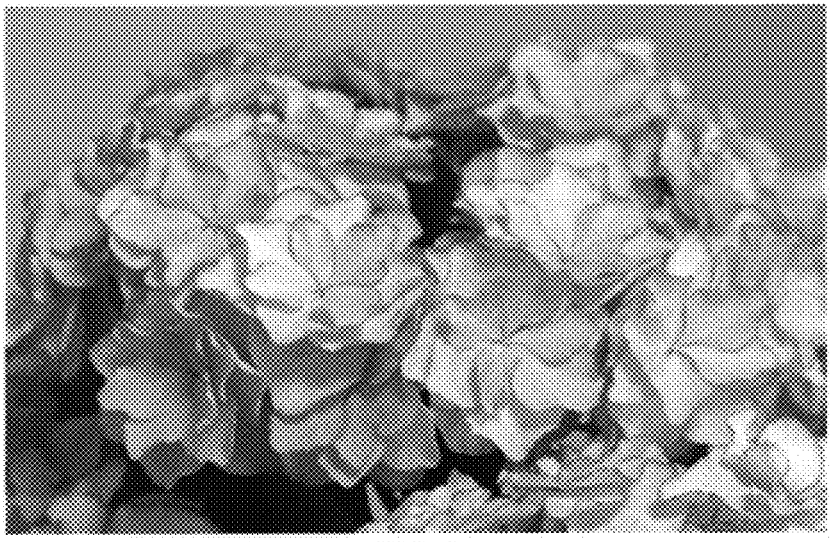
FIG. 2 illustrates an inflorescence with fully-open florets of 'Keiko'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2016 under natural light conditions in Iyo, Japan.

The following descriptions and measurements describe approximately one-year old plants produced from softwood cuttings from stock plants and grown under conditions comparable to those used in commercial practice. The plants were grown in one-gallon containers in a poly-covered greenhouse in Kiryu-shi, Japan. Plants were given one pinch at transplant. Day temperatures ranged from a high of 97° F. (36° C.) to a low of 43° F. (6° C.). Night temperatures ranged from a high of 77° F. (25° C.) to a low of 25° F. (−4° C.). Greenhouse light levels of 30,000 lux to 100,000 lux were maintained during the day. No supplemental lighting was provided. Measurements and numerical values represent averages of typical plants.

Botanical classification: *Hydrangea macrophylla* cultivar Keiko.

Parentage:

*Female parent*.—Proprietary *Hydrangea macrophylla* breeding selection coded KD10, not patented.

*Male parent*.—Proprietary *Hydrangea macrophylla* breeding selection coded K15, not patented.

Propagation:

*Type cutting*.—Softwood.

*Time to initiate roots*.—Approximately 20 to 25 days.

*Time to produce a rooted cutting*.—Approximately 30 to 35 days.

*Root description*.—Medium thickness, fleshy, white, NN155D.

*Rooting habit*.—Moderate branching, moderately dense.

Plant description:

*Commercial crop time*.—Approximately 16 to 18 weeks from a rooted cutting to finish in a 18 cm pot.

*Growth habit and general appearance*.—Deciduous shrub, moderately vigorous, compact-upright.

*Hardiness*.—USDA Zone 5 (−20° F. to −15° F.).

*Heat tolerance*.—Regularly tolerates temperatures as high as 38° C. in the summer.

*Size*.—Height from soil level to top of plant plane: Approximately 45.0 cm. Width: Approximately 50.0 cm.

*Branching habit*.—Freely branching. Pinching enhances branching. Quantity of lateral branches per plant: Approximately 5.

*Branch*.—Shape: Rounded. Strength: Strong. Length to base of inflorescence: Approximately 25.0 cm. Diameter: Approximately 6.6 mm. Length of central internode: Approximately 7.5 cm. Texture of young stem: Glabrous. Texture of mature stem: Woody. Color of young stem: 144A. Color of mature stem: 165C.

*Lenticels*.—Quantity per internode: Approximately 50. Shape: Round to elliptic. Size: Approximately 1.0 mm to 6.3 mm. Color: N79B.

Foliage description:

*General description*.—Quantity of leaves per lateral branch: Approximately 8. Fragrance: Not detected. Form: Simple. Arrangement: Opposite.

*Leaves*.—Aspect: Flat. Shape: Elliptic. Margin: Serrated. Apex: Acuminate. Base: Rounded. Venation pattern: Pinnate. Length of mature leaf: Approximately 7.0 cm to 9.0 cm. Width of mature leaf: Approximately 5.0 cm to 7.0 cm. Texture of upper and lower surfaces: Coriaceous, glabrous. Color of upper surface of young foliage: N137B and venation 146C. Color of lower surface of young foliage: 138B and venation 145C. Color of upper surface of mature foliage: N137A and venation N144D. Color of lower surface of mature foliage: 138A and venation 145B.

*Petiole*.—Length: Approximately 2.2 cm. Diameter: Approximately 3.2 mm. Texture: Glabrous. Color: 145C.

Flowering description:

*Flowering habit*.—Seasonal, mid-May to June in Japan.

*Lastingness of individual inflorescence on the plant*.—Approximately one month.

Inflorescence description:

*General description*.—Type: Terminal compound corymb, modified lacecap in form comprised of a center region of fertile florets surrounded by an outer ring of double-type sterile florets. Quantity per plant: Approximately 5. Fragrance: Not detected. Aspect: Facing upward and outward. Height: Approximately 10.0 cm. Width: Approximately 22.0 cm. Quantity of fertile florets per inflorescence: 250. Quantity of sterile florets per inflorescence: Approximately 30 as double-lacecap type, and approximately 30 as modified from center.

*Peduncle*.—Strength: Strong. Shape: Rounded. Length: Approximately 7.0 cm. Diameter: Approximately 3.2 mm. Texture: Sparsely pubescent with appressed hairs. Color: 143A.

Floret description:

*General description*.—Type: Double-type, sterile and fertile florets.

*Sterile florets, bud just before opening*.—Shape: Flattened. Length: Approximately 4.5 mm. Diameter: Approximately 3.0 mm. Color: N66A with center of NN155B.

*Sterile florets*.—Depth: Approximately 3.3 cm. Diameter: Approximately 7.0 cm. Corolla: 3 vestigial structures approximately 1.0 mm in length and 0.3 mm in diameter. Diameter: Approximately 1.4 mm. Calyx: Approximately 10 to 15 sepals. Shape: Rotate, cruciform. Diameter: Approximately 7.0 cm.

*Sepals, sterile florets*.—Shape: Broadly ovate. Margin: Crenate. Apex: Rounded. Base: Attenuate. Length: Approximately 1.4 cm to 3.7 cm. Width: Approximately 1.0 cm to 3.7 cm. Texture of upper and lower surfaces: Glabrous. Color of upper surface when first open: NN155B with margins of N66C. Color of lower surface when first open: NN155C with margins of N66B. Color of upper surface when fully open: 69C with margins of 68B. Color of lower surface when fully open: 69D with margins of 68B.

*Pedicel, sterile florets*.—Strength: Strong. Aspect: Approximately 30° from peduncle axis. Length: Approximately 4.0 cm. Diameter: Approximately 2.6 mm. Texture: Sparsely pubescent with appressed hairs. Color: 69D with lenticles of N66B.

*Fertile florets, bud just before opening*.—Shape: Globular. Length: Approximately 3.0 mm. Diameter: Approximately 2.2 mm. Color: 142B.

*Fertile florets*.—Depth: Approximately 3.8 cm. Diameter: Approximately 7.2 cm. Corolla: 0 to 6 petals. Shape: Ovate. Diameter: Approximately 3.0 mm. Calyx: Up to 3 vestigial sepals. Shape: Ovate. Diameter: Approximately 3.0 mm.

*Petals, fertile florets*.—Shape: Ovate. Margin: Entire. Apex: Acute. Base: Truncate. Length: Approximately 3.3 mm to 6.9 mm. Width: Approximately 1.4 mm to 6.3 mm. Texture of upper and lower surfaces: Glabrous. Color of upper surface: 69D. Color of lower surface 142C.

*Sepals, fertile florets*.—Shape: Ovate. Margin: Entire. Apex: Acute. Base: Truncate. Length: Approximately 3.1 mm. Width: Approximately 1.2 mm. Texture of upper surface: Glabrous. Texture of lower surface: Sparsely pubescent. Color of upper surface: 143C. Color of lower surface 143B.

*Pedicel, fertile florets*.—Strength: Strong. Aspect: Erect. Length: Approximately 2.6 mm. Diameter: Approximately 0.9 mm. Texture: Sparsely pubescent with appressed hairs. Color: 145B.

*Reproductive organs*.—Observed in fertile florets. Androecium: Not observed. Gynoecium: Pistil quantity: 1 per floret. Pistil length: Approximately 2.5 mm. Stigma shape: Round, 3 to 4 lobed. Stigma color: 154C. Style length: Approximately 1.2 mm. Style color: 154C. Ovary length: Approximately 1.5 mm. Ovary texture: Sparsely pubescent with appressed hairs. Ovary color: 144D.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'Keiko', substantially as herein illustrated and described.

* * * * *